US006309670B1

(12) United States Patent
Heidaran et al.

(10) Patent No.: US 6,309,670 B1
(45) Date of Patent: *Oct. 30, 2001

(54) COLLAGEN-POLYSACCHARIDE MATRIX FOR TREATMENT OF BONE TUMORS

(75) Inventors: Mohammad Heidaran, Los Gatos; Robert C. Spiro, Half Moon Bay, both of CA (US)

(73) Assignee: Orquest, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/324,792

(22) Filed: Jun. 3, 1999

Related U.S. Application Data

(63) Continuation-in-part of application No. 09/007,731, filed on Jan. 15, 1998, now Pat. No. 5,972,385, which is a continuation-in-part of application No. 08/783,650, filed on Jan. 15, 1997, now Pat. No. 5,866,165.

(51) Int. Cl.[7] ............ A61K 9/10; A61K 47/42; A61K 47/36
(52) U.S. Cl. ............ 424/486; 424/484
(58) Field of Search ............ 424/484, 486; 514/773, 777

(56) References Cited

U.S. PATENT DOCUMENTS

| | | |
|---|---|---|
| 4,517,295 | 5/1985 | Bracke et al. . |
| 4,931,546 | 6/1990 | Tardy et al. . |
| 5,128,326 | 7/1992 | Balazs et al. . |
| 5,597,578 * | 1/1997 | Brown et al. . |

OTHER PUBLICATIONS

Amiel, et al., 1985, "Rib Perichondrial Grafts for the Repair of Full–Thickness Articular–Cartilage Defects," *J. Bone Joint Surg.* 67A:911–920.

Blein–Sella, O., et al., 1995, "Rabbit Articular Chondrocyte Functional Toxicity Test," *Methods Mol. Biol.* 43:169–75.

Dietz, U., et al., 1993, "Alterations of Collagen mRNA Expression During Retinoic Acid Induced Chondrocyte Modulation: Absence of Untranslated $\alpha 1(I)$ mRNA in Hyaline Chondrocytes," *J. Cell Biol.* 52(1):57–68.

Kuettner, K.E., et al. 1992, "Biochemistry of Articular Cartilage in Health and Disease," *Clin. Biochem.* 25:155–63.

Lee, M.K., et al., 1991, "Analysis of affinity and structural selectivity in the binding of proteins to glycosaminoglycans: Development of a sensitive electrophoretic approach" *Proc. Natl. Acad. Sci USA* 88 (7):2768–72.

Sandell, L.J., et al., 1991, "Alternatively Spliced Type II Procollagen mRNAs Define Distinct Populations of Cells during Vertebral Development: Differential Expression of the AMino–Propeptide," *J. Cell Biol.* 114 (4):1307–19.

Schmid, T.M., et al., 1985, "Immunohistochemical Localization of Short Chain Cartilage Collagen (Type X) in Avian Tissues," *J. Cell Biol.* 100:598–605.

Spiro, R.C., et al., 1991, "Uncoupling of Chondroitin Sulfate Glycosaminoglycan Synthesis by Brefeldin A," *J. Cell. Biol.*, 115 :(5)1463073

Thyberg and Moskalewski, 1979, "Bone Formation in Cartilage Produced by Transplanted Epiphyseal Chodrocytes," *Cell Tissue Res.* 204(1): 77–94.

Wong and Cohn, 1975, "Target cells in bond for parathormore and calcitonin are different: Enrichment for each cell type by sequential digestion of mouse calvaria and selective adhesion to polymeric surfaces," *Proc. Natl. Acad. Sci. USA* 72:3167–71.

* cited by examiner

Primary Examiner—Edward J. Webman
(74) Attorney, Agent, or Firm—Fish & Richardson, PC

(57) ABSTRACT

A method of treatment for bone tumors comprising administering a matrix comprising collagen, a polysaccharide and a differentiation factor is provided. A polysaccharide is reacted with an oxidizing agent to open sugar rings on the polysaccharide to form aldehyde groups. The aldehyde groups are reacted to form covalent linkages to collagen.

19 Claims, 2 Drawing Sheets

Growth Inhibition of a Combination of CN:HA matrix/TGFb

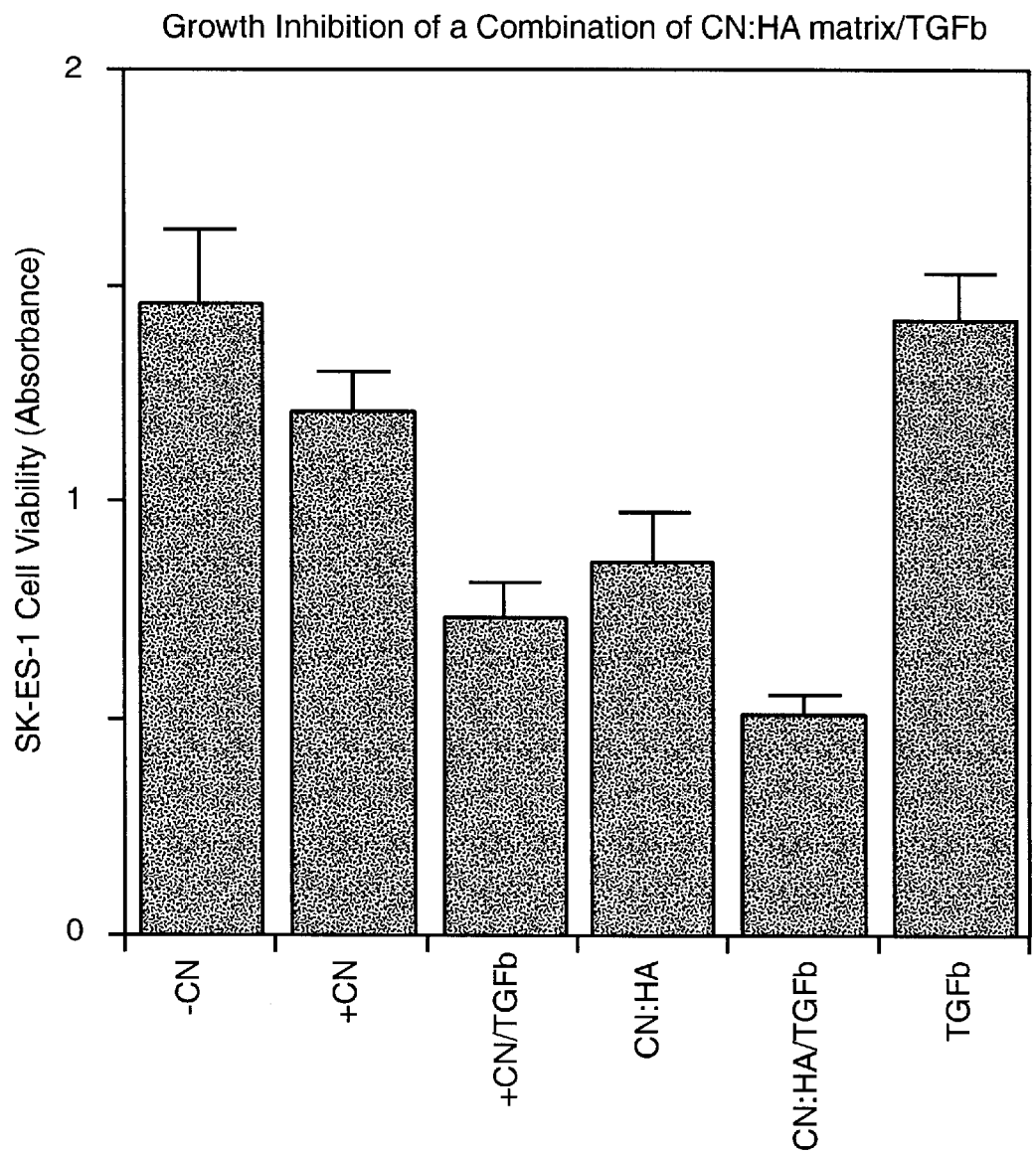
FIG._1

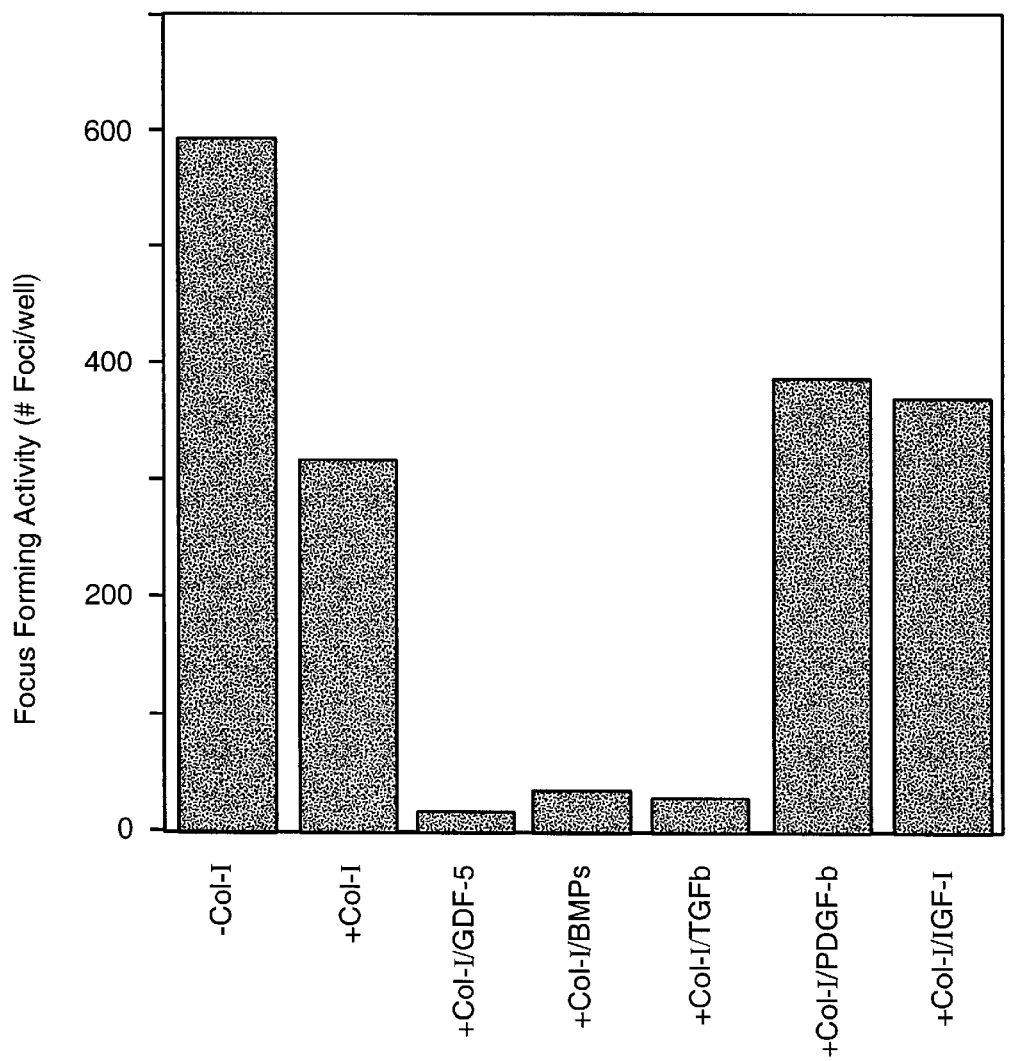
FIG._2

COLLAGEN-POLYSACCHARIDE MATRIX FOR TREATMENT OF BONE TUMORS

CROSS REFERENCE TO RELATED APPLICATIONS

This is a continuation-in-part of U.S. patent application Ser. No. 09/007,731, filed Jan. 15, 1998, now U.S. Pat. No. 5,972,385 which is a continuation-in-part of U.S. patent application Ser. No. 08/783,650, filed Jan. 15, 1997, now U.S. Pat. No. 5,866,165.

FIELD OF THE INVENTION

The present invention relates to crosslinked collagen-polysaccharide matrices for the treatment of bone tumors and methods of treatment using the matrices. The present invention provides a crosslinked collagen-polysaccharide matrix that is administered together with a differentiation factor for treatment of bone tumors.

BACKGROUND OF THE INVENTION

Bone tumors represents the major cause of morbidity and mortality associated with many types of cancer. Currently, the conventional procedure for treatment of bone tumor involves a combination of surgical resection, radiation and/or chemotherapy. Despite recent advances in the management of neoplastic diseases, the prognosis and quality of life for patients with aggressive bone tumors undergoing such multimodal therapies is still poor. Current experimental approaches for treatment of tumors are focused on the localized delivery of inhibitors of growth and neovascularization.

Collagens and glycosaminoglycans are two classes of biomaterials suited for use in bone regeneration. Collagen based matrices have been used in bone grafting. Type I collagen has good cell adhesive properties, in particular, for bone forming osteoblast cells.

Hyaluronic acid is a natural component of the extracellular matrix in many tissues including bone, and it is readily sterilized, is biodegradable and can be produced in a wide range of consistencies and formats. It is generally biocompatible and its resorption characteristics can be controlled by the manipulation of monomers to polymer forms, most commonly through the esterification of the carboxylic groups of the glucuronic acid residues.

The TGF-$\beta$ superfamily consists of a large group of growth factors that exert profound influences on cellular morphology and the growth and differentiation of many cell types both in vitro and in vivo. The members of this superfamily are distinguished from other growth factors based on their unique ability to induce cell cycle arrest and the differentiation of mesenchymal cells and uncommitted cells during embryogenesis (Massague, J. S., Cheifetz, F. T., Andres, J. L. Ann. NY. Acad. Sci. 593:59–72, 1990). The mechanism of TGF-$\beta$ induced cell cycle arrest is among the most intensively studied over the last decade. Members of this family include TGF-$\beta$1, $\beta$2 and $\beta$3, the Bone Morphogenetic Proteins (BMPs), and growth and differentiation factors (GDFs).

SUMMARY OF THE INVENTION

The present invention relates to methods of using a crosslinked collagen-polysaccharide matrice comprising a differentiation factor in the treatment of bone tumors. The present invention is based, in part, upon the unexpected finding that a collagen-polysaccharide matrix containing a differentiation factor inhibits growth of osteosarcoma cell lines more potently than the factor alone and the collagen-polysaccharide matrix alone. The present invention is also based upon the unexpected in vitro finding that a collagen-polysaccharide matrix containing TGF-$\beta$ exhibits more potent anti-growth property than a combination of soluble collagen and TGF-$\beta$. The present invention is also based upon the finding that a collagen-polysaccharide matrix containing TGF-$\beta$ elicits opposite responses in normal osteoblasts versus tumor cells.

Accordingly, the present invention provides a method for the treatment of bone tumors comprising the step of administering a matrix comprising (1) collagen covalently crosslinked to an exogenous polysaccharide, wherein said polysaccharide is crosslinked to said collagen through oxidized sugar rings on said polysaccharide which form covalent linkages to said collagen, and (2) a differentiation factor at a site of desired treatment As used in this discussion, an exogenous polysaccharide refers to a free polysaccharide.

In one embodiment, the matrix comprising the differentiation factor is implanted in a defect created after surgical resection of the tumor. In another embodiment, the matrix is injected in an osteolytic lesion.

The collagen used in a matrix of the present invention may be purified, native or modified collagen of any type. In one embodiment, the collagen is Type I collagen and in another embodiment, the collagen is Type II collagen.

The type of polysaccharides which can be used include hyaluronic acid, chondroitin sulfate, dermatan sulfate, keratan sulfate, heparan, heparan sulfate, dextran, dextran sulfate, alginate, and other long chain polysaccharides. In a preferred embodiment, the polysaccharide is hyaluronic acid.

The type of differentiation factor which can be used in the present invention include members of the TGF-$\beta$ superfamily including, the Bone Morphogenic Proteins (BMPs); growth and differentiation factors (GDFs) and TGF-$\beta$1, B2 and B3. In a preferred embodiment, a crosslinked collagen-hyaluronic acid matrix comprising TGF-$\beta$1 is used in the treatment of bone tumors.

The ratios of the collagen to polysaccharide can be varied to change both the physical and biological properties of the matrix. A higher proportion of collagen will result in a more porous sponge-like matrix. A higher proportion of polysaccharide will result in a more gel-like matrix.

As used in this discussion, "treatment of bone tumor" refers to minimizing or eliminating the presence of tumor cells at the site of administration. Bone tumor includes osteosarcoma and neuroectodermal tumors. Administration encompasses injection of a gel-like matrix as well as implantation of a sponge like matrix.

As used in this discussion, "repair" is defined as growth of new tissue. The new tissue may or may not be phenotypically or genotypically identical to the original lost tissue. As used herein, "regeneration of tissue" means that the new tissue grown is identical to the lost tissue. Tissue repair can also be the result of replacing lost tissue with non-identical tissues. The basic cellular properties involved in repair include adhesion, proliferation, migration and differentiation.

By "conduction", it is meant that the host tissue, e.g., bone, grows by extension of existing tissue onto or into the crosslinked collagen-polysaccharide matrix. In conduction, repair cells move onto and into the matrix to synthesize and remodel new tissue identical to the surrounding host tissue. By induction, it is meant that the growth and differentiation of progenitor repair cells is stimulated. These progenitor cells go on to synthesize and remodel new tissue to be continuous with the surrounding host tissue.

BRIEF DESCRIPTION OF THE DRAWING

FIG. 1 illustrates the growth inhibition of an osteosarcoma line using of a combination a collagen-hyaluronate matrix comprising TGF-β.

FIG. 2 illustrates the inhibition of focal transformation of the osteosarcoma cell line Sk-ES-1 in vitro by differentiation growth factor(s).

DESCRIPTION OF THE PREFERRED EMBODIMENTS

The method of preparing a matrix of the present invention comprises the steps of opening sugar rings on an exogenous polysaccharide and oxidizing terminal hydroxy groups to aldehydes using, for example, sodium or potassium periodate as a selective oxidizing agent. The amount of aldehyde groups produced in this manner can be stoichiometrically controlled. Typically, from about 1% to 50% of the rings can be opened in this manner. More preferably about 1% to 5% of the rings are opened to form the aldehyde groups. These aldehyde groups can form covalent crosslinks with the collagen at amine sites on the collagen peptide chains. Since the aldehyde groups are formed in situ without the addition of a separate cross-linking compound, the intermolecular distance between the backbone of the polysaccharide chain and the collagen chain which is crosslinked to it is believed to be less than the corresponding distance using a crosslinking compound. Accordingly, the polysaccharide and collagen backbones are relatively closely bound, which produces an advantageous structure for the purpose of providing a matrix that supports, conducts or induces the growth of bone.

The starting material for producing the collagen may be purified, native collagen or modified collagen of any type. A preferred collagen for bone growth is Type I collagen. The collagen may be crosslinked or non-cross-linked, but it is preferred that the collagen be non- crosslinked to provide more accessibility to side groups for crosslinking to the polysaccharide aldehyde groups.

Typically, the polysaccharide will have an average molecular weight of about 1,000 to 10,000,000 DA.

The reagents for opening sugar rings on the exogenous polysaccharide may be any selective oxidizing agent which oxidizes a terminal hydroxyl group to an aldehyde, such as potassium or sodium periodate. Other reagents include specific sugar oxidases.

The preferred polysaccharide is hyaluronic acid. The relative proportion of polysaccharide to collagen will impart various physical and biological characteristics to the matrix. The proportion of polysaccharide to collagen may be characterized on a molar ratio basis or on a weight ratio basis. Typically, the ratio by weight of collagen to polysaccharide is from 99:1 to about 1:99. This represents an approximate molar ratio of 99.9:0.1 to 1:9, respectively, assuming an average molecular weight of 1,000,000 daltons for hyaluronic acid and 100,000 daltons for collagen. The molar ratio may vary depending on the actual molecular weight of the polysaccharide and collagen used. In a preferred embodiment disclosed herein, the ratio by weight of collagen to polysaccharide is from 9:1 to about 1:9.

The ratios of the collagen to polysaccharide can be varied to change both the physical and biological properties of the matrix. Biologically, a higher proportion of Type I collagen will more closely mimic the composition and architecture of bone. Bone forming cells will interact with specific cell adhesion sites on collagen and will divide, migrate and differentiate to form new bone.

The TGF-β superfamily consists of a large group of growth and differentiation factors that exert profound influences on cellular morphology and the growth and differentiation of many cell types both in vitro and in vivo. The members of this superfamily are distinguished from other growth factors based on their unique ability to induce cell cycle arrest and the differentiation of mesenchymal cells and uncommitted cells during embryogenesis (Massague, J. S., Cheifetz, F. T., Andres, J. L. *Ann. NY. Acad. Sci.* 593:59–72, 1990). Members of this family, including TGF-β, Bone Morphogenetic Proteins (BMPs), and growth and differentiation factors (GDFs).

Differentiation factor preparations are obtained either commercially or isolated and purified from tissue or from recombinant sources. TGF-β1 is supplied by R&D Systems (Minneapolis, Minn.). Partially purified and active GDF-5 and crude BMPs can be isolated according to previously published techniques (Nishitoh et al., *J. Biol. Chem.* 271:21345–21352, 1996 and Seyedin et al. *Proc. Natl. Acad. Sci. U.S.A* 82:2267–2271 (1985).

A preferred method of making a collagen-polysaccharide matrix of the present invention comprises the steps of oxidizing an exogenous polysaccharide to form a modified exogenous polysaccharide having aldehyde groups, and reacting the modified exogenous polysaccharide with collagen under conditions such that the aldehyde groups covalently react with collagen to form a crosslinked matrix. In a preferred embodiment, a preformed, lyophilized collagen-polysaccharide matrix is contacted with a solution comprising differentiation factor, allowed to fully hydrate with the solution and then lyophilized.

Bone tumors may be classified into two categories based upon their physiopathological origin. These include malignant tumors arising from either the musculoskeletal system and metastases from primary tumors of other origins. Osteosarcoma and Ewing sarcoma represent the most common types of bone tumor and occur mainly in children and adolescents. Osteosarcomas represent 90% of primary malignant bone tumors and are composed of neoplastic spindle cells and osteoblasts that produce immature bone. In contrast, Ewing sarcoma accounts for only about 6–10% of primary malignant bone tumors. Ewing sarcoma cells are small, regular, and round and exhibit an undifferentiated, primitive neural phenotype (Yunis, E. J. *Am. J. Surg. Pathol.*, 10:54–62, 1986). Ewing sarcoma usually arises in the diaphysis of long tubular bones, especially the femur and the flat bones of the pelvis.

The matrices according to the present invention may be formed into any shape by lyophilization, or wet-laying and air drying in molds of the desired shape. The lyophilized or wet-layed material having a high proportion of polysaccharides may also be formed into viscous gels for injection or direct application into a bone void or bone defect that occurs as a result of a surgical resection or osteolytic lesion. In a preferred embodiment, the matrices are loaded with active differentiation or growth factor using sterile admix procedure followed by lyophilization. Sterile, lyophilized matrices are fully hydrated with growth factor containing solutions made at concentrations required to yield the desired weight per volume dose. Hydrated matrices are then lyophilized and stored desiccated prior to implantation. In another embodiment, the differentiation or growth factor may be covalently cross-linked to the polyaldehyde form of the hyaluronic acid.

The amount of differentiation factor incorporated into the collagen-polysaccharide matrix will generally be in the range of $10^{-2}$ to $10^4$ micrograms/milligrams matrix. They are incorporated into the matrix by aseptic addition followed by lyophilization.

The usefulness of the matrices according to the present invention can be shown by both in vitro and in vivo tests. For in vitro evaluation, candidate matrices about 45 mm$^3$ in size are injected with $2\times10^5$ bone tumor cells, such as the SK-ES-1 cell line. The cell-seeded matrices are placed in 24 well TransWell plates (Costar) and cultured in DMEM containing 10% FBS and the specific differentiation factor at concentrations of 10 and 100 ng/ml. After 21–28 days, the growth properties of the tumor cells are monitored using a mitogenic or MTS assay. The expression of differentiation markers is examined at the protein level using an alkaline phosphatase activity assay and immunoassays for osteocalcin. The effect of matrices on the expression of genetic markers for osteoblastic differentiation is performed based on semi-quantitative RT-PCR analysis using specific primers to alkaline phosphatase, type I collagen, and osteocalcin.

For in vivo evaluation, the SK-ES-1 cell line or normal osteoblastic cells are cultured for three weeks in candidate matrices supplemented with or without differentiation factor. Samples of composite matrices containing no cells, normal osteoblasts or SK-ES-1 tumor cells are then be subcutaneously implanted into the back of male athymic nude mice (Ncr nu/nu). After a predetermined amount of time (3–6 weeks), matrices are explanted and the tumor weight and volume will be determined. The explant samples are fixed in a 10% formaldehyde solution, replaced with ethanol and embedded in paraffin. The samples are sectioned to 10 um in thickness and stained with Hematoxylyn and Eosin (H&E) (Pinski et al., 1995, *Natl. Cancer Inst.* 87:1787–1794).

In an additional in vivo animal model, athymic nude mice (nu/nu, NCR Charles River) are injected subcutaneously with a determined number of cells from the SK-ES-1 cell line. For preparation of cells to be injected, SK-ES-1 cells are cultured for 3 weeks in the presence or absence of collagen (CN) and TGF-β1 (100 ng/ml) as described infra. The indicated number of cells will be harvested, washed, and injected subcutaneously in nude mice. The animals are weighed regularly and tumor formation is monitored by observation, palpitation and measurement of tumor size. Following the observation period of 6 weeks, the mice are euthanized and subjected to macroscopic necropsy. The tumor masses are removed, weighed and measured. Histological sections are prepared and stained with hematoxylin and eosin using standard protocol and examined. The tumor masses are characterized histologically and the effects assessed. Tumor pieces are subjected to immunohistological evaluation.

Cell adhesion and proliferation on the matrix are monitored using an MTS assay (Cory et al., 1991, Cancer Commun. 3:207) that can measure cell number and viability based on mitochondrial activity. Tumor cells or bone progenitor cells are cultured on matrices for 6–18 hrs. in the presence or absence of serum for adhesion analysis and for 1–2 weeks for proliferation assessment.

For cell migration testing, matrices are coated or fitted onto porous Trans-well membrane culture inserts (Corning). Tumor cells or bone progenitor cells are seeded on top of the matrices in the upper chamber of the Trans-well and a chemoattractant (growth factor, PDGF) placed in the bottom chamber. After 12–18 hrs of culture the cells that have migrated through the matrix to the bottom side of the Trans-well membrane are quantitated by the MTS assay. Matrices are removed from the upper chamber and processed histologically to assess degree of infiltration.

The analysis of differentiation markers relevant to osteogenesis are evaluated at both the protein and transcriptional level. The specific markers that may be analyzed include: 1) Type I collagen; 2) Aggrecan proteoglycan; 3) Type IX, X and XI collagen; 4) Type II collagen; 5) Osteocalcin; 6) Osteopontin; 7) Fibronectin (EDA, EDB isoformns); 8) Decorin proteoglycan; 9) Link protein; 10) thrombospontin; 11) Biglycan proteoglycan; and 12) Alkaline phosphatase. Differentiation may be measured by Northern/PCR analysis, Western blotting or by metabolic cell labeling.

For Northern/PCR analysis, RNA are isolated by standard procedures from cells that have been cultured on composite matrices. Time course tests may be used to determine optimal culture periods that range from 1 to 6 weeks depending on the cell type. The isolated RNA is analyzed by Northern gel and hybridization techniques with specific cDNA or PCR amplified probes. Northern analysis is quantified by densitometric scanning of autoradiographs and normalization to housekeeping gene signals (G3PDH). Northern analysis may be supplemented with quantitative PCR analysis using primers generated from the published cDNA sequences of the genes to be analyzed.

For Western blotting, solubilized protein lysates are isolated from cells cultured on composite matrices by standard techniques (Spiro R. C., et al., 1991, J. Cell. Biol., 115:1463–1473). After the lysis of cells the matrices are extracted in stronger denaturants (8 M urea, GnHCL) to remove and examine matrix-bound or incorporated proteins. Protein samples are analyzed by standard Western blotting techniques using specific polyclonal or monoclonal antibodies.

For metabolic cell labeling, cells cultured on a composite matrix are metabolically radiolabeled with 35SO4, 35S-methionine or 3H/14C-labeled amino acids by standard techniques (Spiro et al., supra). Solubilized cellular and matrix-associated proteins are quantitatively immunoprecipitated with antibodies specific for the protein of interest and analyzed by SDS-PAGE (Spiro et al., supra). Quantitation of results are performed by densitometric scanning of autoradiographs and signals will be normalized to either cell equivalents or to a house-keeping protein such as actin.

An alternative approach is to use radiolabeled or biotinylated proteins for the binding analysis. Serum proteins may be biotinylated prior to incubation with the composite matrices and then developed with avidin-based reagents. Both approaches allow the visualization of matrix-associated components without the interference of the scaffold collagen protein.

For the in vivo tests, the matrices are evaluated for the capabilities for supporting osseous healing in a rat cranial defect model by implantation into a 5 mm by 3 mm defect created in the parietal bone of 6 weeks old male Sprague-Dawley rats. The defects are evaluated at 28 days by radiographic and histologic analysis.

The matrices of the present invention may be used for the treatment of bone tumor including defects associated with surgical resection or osteolytic lesions. The matrices according to the present invention may be administered through implantation, direct application or injection depending on the intended application of the matrix, the physical properties of the matrix and the ratio by weight of collagen to polysaccharide in the matrix. The present invention encompasses the use of a matrix of the present invention in the treatment of sarcomas and carcinomas, including metastatic bone tumor, osteosarcoma, and Neuroectodermal tumors, such as, Ewing Sarcoma and Neuroblastoma.

As will be understood by those of skill in the art the amount of matrix to be administered to treat bone tumors will depend upon the extent and severity of the disease. In general, the tumor-growth inhibiting amounts will be a matrix containing $10^{-2}$ to $10^4$ micrograms of differentiation factor per milligram of matrix. As will also be understood by those of skill in the art, the cost, safety, and desired differentiation factor release profile will dictate the type and amount of growth factor that is loaded onto the matrix. The following examples are provided for purposes of illustration and are not intended to limit the invention in any way.

EXAMPLE 1

This example illustrates the production of a variety of matrices. In the following matrices, Type I collagen was used as a raw material. Semed F collagen (Type I, insoluble) and Semed S collagen (Type I, acid soluble) were from Kensey-Nash. Hyaluronic-polyaldehyde, dextran-polyaldehyde, dextran sulfate/polyaldehyde, and chondroitin sulfate/polyaldehyde were prepared by oxidation of the related polysaccharide with reagent grade sodium periodate.

The matrix in this case was based on the reaction of protein amine residues on the collagen with the active aldehyde groups generated on the sugar rings of the polysaccharides. Matrices with various surface properties and biological activity are synthesized by controlling the ratios of the collagen to the polysaccharides, the type of collagen, the types of polysaccharides, as well as the density of the aldehyde groups generated on the polysaccharides.

Semed F collagen (8.1 parts) and Semed S collagen (0.9 part) were dispersed in a hyaluronate/polyaldehyde solution (1 part, 5% of the repeat units were oxidized: pH 3–3.5) containing 10 mM sodium cyanoborohydride (NaCNBH$_3$) in a heavy duty blender at low speed for 10 seconds followed by high speed for another 5 seconds. The slurry (solids concentration: 28 mg/ml) was poured into a mold, incubated at ambient temperature for 24 hours and lyophilized. This formed a sponge which was washed several times in distilled water to completely remove the NaCNBH$_3$. The washed sponge was then lyophilized.

The above procedure was followed to make other matrices using the starting materials as follows:

| | |
|---|---|
| Semed F collagen (0.9 part) Semed S collagen (0.1 part) | Hyaluronate/polyaldehyde solution (1 part, 5% of the repeat units oxidized) Solids concentration: 15 mg/ml |
| Semed F collagen (0.9 part) Semed S collagen (0.1 part) | Hyaluronate/polyaldehyde solution (2 parts 5% of the repeat units oxidized) Solids concentration: 15 mg/ml |
| Semed F collagen (0.9 part) Semed S collagen (0.1 part) | Hyaluronate/polyaldehyde solution (4 parts 5% of the repeat units oxidized) Solids concentration: 15 mg/ml |
| Semed F collagen (0.9 part) Semed S collagen (0.1 part) | Hyaluronate/polyaldehyde solution (4 parts 1% of the repeat units oxidized) Solids concentration: 15 mg/ml |
| Collagen Type II (9 parts) | Hyaluronate/polyaldehyde solution (1 part, 5% of the repeat units oxidized) Solids concentration: 15 mg/ml |

-continued

| | |
|---|---|
| Collagen Type II (1 part) | Hyaluronate/polyaldehyde solution (1 part, 5% of the repeat units oxidized) Solids concentration: 15 mg/ml |
| Semed F collagen (7 parts) Collagen Type II (2 parts) | Hyaluronate/polyaldehyde solution (1 part, 5% of the repeat units oxidized) Solids concentration: 15 mg/ml |
| Semed F collagen (8.1 parts) Semed S collagen (0.9 part) | Dextran/polyaldehyde solution (1 part, 5% of the repeat units oxidized) Solids concentration: 28 mg/ml |
| Semed F collagen (8.1 parts) Semed S collagen (0.9 part) | Dextran sulfate/polyaldehyde (1 part, 5% of the repeat units oxidized) Solids concentration: 28 mg/ml |
| Semed F collagen (8.1 parts) Semed S collagen (0.9 part) | Chondroitin sulfate/polyaldehyde (1 part, 5% of the repeat units oxidized) Solids concentration: 28 mg/ml |
| Semed F collagen (0.9 part) Semed S collagen (0.1 part) | Hyaluronate/polyaldehyde solution (4 parts 5% of the repeat units oxidized) Solids concentration: 15 mg/ml |

EXAMPLE 2

This example illustrates the assays used to assess matrices for stimulating differentiation of tumor cell lines in vitro. The matrices are assessed based upon 1) their ability to stimulate the differentiation of tumor cell lines (Plate assay); and 2) their ability to inhibit the anchorage-independent growth of tumor cells (Soft Agar assay). The ability to induce growth arrest and differentiation are be assessed based on changes in 1) cellular morphology of the tumor cell lines; 2) mitogenic activity; and 3) expression of gene markers for osteoblastic differentiation.

Materials

Type I collagen used is bovine dermal collagen manufactured known by methods or purchased from Collagen Corp. (Palo Alto, Calif.). TGF-β is purchased from R&D Systems (Minneapolis, Minn.). Partially purified and active GDF-5 and crude BMPs can be isolated according to previously published techniques (Nishitoh, et al. *J. Biol. Chem.* 271:21345–21352, 1996 and Seyedin et al. *Proc. Natl. Acad. Sci. U.S.A* 82:2267–2271, (1985).

The activity of crude BMPs and GDF-5 is monitored based on their ability to enhance bone formation in situ. The cell lines, Human osteosarcoma SK-ES-1 and MNNG/HOS are utilized to determine the inhibitory effects of candidate matrix /differentiation factor combinations. The SK-ES-1 cell line undergoes a dramatic change in cellular morphology in response to antiproliferative growth factors. This change in cellular morphology is marked by a reduction in the number of transformed foci which correlates directly to the loss of anchorage-independent growth and a decrease in tumorogenicity (Freedman, V. H., and Shin, S.: *Cell* 3:355–359, 1974.). Fetal Rat Calvarial (FRC) cells are utilized as normal osteoblasts. The cells are maintained in DMEM with non-essential amino acids, supplemented with 10% FBS, 2 mM glutamine, 50 units/ml penicillin, 50 ug/ml streptomycin, and 5 ug/ml gentamicin. The cells are incubated at 37° C in a humidified atmosphere of 95% air, 5% CO$_2$ and subcultured weekly using 0.05% trypsin and 0.53 mM EDTA.

Plate Assay

Tissue culture plates are coated for 3 hours at 37° C with a solution of PBS or 0.1 M sodium bicarbonate containing various protein substrates (?et al. *J.Cell Physiol.* 153:256–365, 1992). Nonadsorbant proteins are removed by rinsing twice with PBS. The tumor cells are seeded in 12-well plates at an initial density of 20–25000 cells/cm$^2$ in DMEM supplemented with 10% FBS. After 12 hours, the media is replaced with DMEM, 1% FBS supplemented with various growth factors including TGF-β GDF-5 and crude BMPs. The ability of other mitogens including Platelet Derived Growth Factor (PDGF), to change the cellular morphology of osteosarcoma cell lines is assessed in parallel as a control.

Focal Transformation Assay

Tumor cell lines, cultured for 3 weeks as described above are fixed using 4% formalin, stained with Giesma and photographed (Heidaran et al. *Oncogene* 5: 1265–1270, 1990). The effect of various growth factor/matrix combinations on the cellular morphology of SK-ES-1 are quantitated based on a reduction in the number of transformed foci. Focal transformation is characterized by a loss of cell to cell contact inhibition that leads to cellular aggregation. The ability of a cell to form foci in vitro correlates well with their ability to undergo anchorage-independent growth in vitro and tumor formation in nude mice (Freedman, V. H., and Shin, S.: *Cell* 3:355–359, 1974 and Heidaran et al. *Oncogene* 5: 1265–1270, 1990).

Soft Agar Assay

For analysis of the effect of different growth factor/ECM combinations on proliferation of tumor cell lines in vitro, SK-E-ES-1 cells ($1 \times 10^5$) are suspended in 0.4% agarose (SeaPlaque) in DME containing 10% calf serum along with various concentrations of ECM proteins. Cells are fed with DME containing 10% calf serum in the presence or absence of indicated growth factors once a week. Colonies are stained with p-iodonitrotetrazolium violet and scored after 2 weeks of culture (Yu et al., 1994, *J. Cell. Biol.* 127: 479–487).

Mitogenic Assay

DNA synthesis is measured in 12-well cell culture plates pre-coated with various ECM proteins prior to cell seeding in the presence of indicated growth factors as described above. After indicated time periods, the cultures are placed in serum free growth medium containing an equal mixture of MCBD 401, LeibovitzÕs L-15 and Ham's F-12 supplemented with 10 nM selenium (Gibco) and 10 ug/ml transferrin (Collaborative Research) and [$^3$HMethyl-thymidine] (2 uCi/ml; Amersham) for 2–4 hours at 37° C. Cells are harvested by washing twice in PBS followed by three washes in cold 5% trichloroacetic acid. Trichloroacetic acid-precipitable radioactivity is solubilized by adding 200 ul of 0.25 M sodium hydroxide followed by addition of 10 ml Biofluor (NEN). Samples are counted in Beckman scintillation counter (Fleming et al. *Oncogene* 7:1355–1359). In parallel, the viability of cells is measured using MTS assays as described previously (1992 Scudiero, D. A. *Cancer Research* 48:4827–4829, 1988). Cell differentiation: The analysis of differentiation markers is performed at the protein and transcriptional level. The specific markers to be analyzed include: 1) type I, II, and X collagen 2) alkaline phosphatase, 3) osteonectin and 4) osteocalcin.

a) Northern/PCR Analysis

RNA is isolated by standard procedures from tumor cell lines that have been cultured for 3 weeks under different experimental conditions. The isolated RNA is analysed by semi-quantitative PCR analysis using primers generated from the published cDNA sequences of the genes to be analyzed. The RT-PCR analysis is supported with Northern gel and hybridization techniques with specific cDNA. Northern analysis is quantified by densitometric scanning of autoradiographs, normalized to a housekeeping gene (G3PDH).

b) Alkaline Phosphatase Activity

Activity is determined at room temperature by a modification of the method of Lowery (Lowry, O. *Meth. Enzymology.* 4:371–372, 1955). The assay mixture contains 0.5 M 2-amino-2-methyl-propanol, 2 nM $MgCl_2$, 7.5 mM diNa-p-nitrophenylphosphate, and 50–100 ul of cell homogenate, containing about 10 ug of protein. The rate of appearance of p-nitrophenol is recorded at 410 nm.

c) Immunoassays for Osteonectin and Osteocalcin

For monitoring the expression of osteonectin and osteocalcin, samples of freeze-dried conditioned media are reconstituted in 100 ul of 50 mM $NH_4HCO_3$, pH=8.0. Osteocalcin and osteonectin levels are measured using a solid phase immunoassay described by Tracey et al. *J. Bone Mineral Res.* 5:451–461,1990.

EXAMPLE 3

This Example illustrates that a combination of a three dimensional matrix comprising collagen (CN), hyaluronate (HA) and TGF-β inhibits growth of the Osteosarcoma cell line SK-ES-1 more potently than a combination of TGF-β and collagen in a monolayer culture.

Materials and Methods

SK-ES-1 osteosarcoma cell line (obtained from the ATCC, Rockville, Md.) was expanded in Dulbeco Eagle Medium (DMEM) supplemented with 10% fetal bovine serum (FBS) using a T75 flask for 5 days. The confluent cells were then washed with PBS/EDTA solution briefly, followed by trypsinization using a mixture of Trypsin/EDTA for 2 minutes at room is temperature. The trypsination experiment was terminated by addition of excess growth media. The cells were then washed and resuspended in the appropriate final volume of growth media. For viability assays, 12 well plates were coated with or without 0.1 mg/ml soluble type I collagen (Collagen Corp., Palo Alto, Calif.) for 2 hours at 37 C. The excess collagen was removed and the harvested cells were either plated at density of $1 \times 10^5$ cells per well or loaded onto the Collagen/HA matrix (24 mm3). SK-ES-1 cells were then cultured for 10 days in the growth media supplemented with or without 100 ng/ml of TGF-β (R&D Systems Minneapolis, Minn.). For quantitation of cell viability, an aliquot of culture media was used for MTS assay.

Results

As illustrated by FIG. 1, the CN-HA/TGF-β combination inhibits growth of osteosarcoma cell line by around 70% as compared to growth of these cells in the presence of TGF-β alone. Also, a combination of CN-HA matrix and TGF-β exhibits more potent anti-growth property than a combination of soluble collagen and TGF-β when used in monolayer culture. Under experimental conditions, TGF-β is not an inhibitor of growth when used in the absence of type I collagen and the CN:HA matrix alone is an inhibitor of SK-ES-1 tumor cell line. These results suggest that the inherent property of CN-HA matrix, i.e. its composition and structure, is necessary for maximal growth inhibition of SK-ES-1 and that this matrix provides a new composition for maximizing the inhibitory effect of TGF-β.

EXAMPLE 4

This Example illustrates the inhibition of focal transformation of SK-ES-1 cell line treated with a combination of Collagen type I and recombinant TGF-β, as well as other members of the TGF-β superfamily.

Twelve well plates were coated overnight with 0.01% (w/v) collagen type I in PBS. After removal of nonadsorbant protein, SK-ES-l cells were plated at a density of $2 \times 10^5$ cell/well in DMDM supplemented with 10% FBS. Cells were then treated with vehicle or TGF-β at 100 ng/ml. Cell cultures were maintained for 21 days in the presence of factor. Plates were then stained with Giesma and photographed. The results indicate that TGF-β acts in synergy with the type I collagen to reduce the number of transformed foci. Under these experimental conditions, type I collagen alone partially inhibits focal transformation and the TGF-β alone fails to reduce focal transformation. Since there is a direct correlation between formation of foci in vitro and tumor formation in vivo, these findings suggest that as matrix composed of type I collagen and TGF-β suppress the growth of Ewing sarcoma in vivo.

In FIG. 2, 12 well plates were coated with type I collagen and used to culture SK-ES-1 cells in the presence of the indicated growth factor for 21 days. Plates were stained with Giesma, photographed and the number of foci were quantitated. Results indicate that the focal transformation of SK-ES-1 can be inhibited by a combination of type I collagen and growth factors belonging to the TGF-β superfamily including GDF-5 and BMPs. Under these conditions, mitogens including PDGF-β and IGF-I failed to stimulate a similar inhibitory effect on the transformation of SK-ES-1 cells. These results suggest that the potent anti-proliferative activity of TGF-β may also be mediated by other members of the TGF-β superfamily.

What is claimed is:

1. A method for the treatment of a bone tumor comprising the steps of administering at a site of desired treatment a matrix comprising:
   a) collagen covalently crosslinked to an exogenous polysaccharide, wherein said polysaccharide is crosslinked to said collagen through oxidized sugar rings on said polysaccharide which form covalent linkages to said collagen; and
   b) a differentiation factor.

2. The method of claim 1, wherein said bone tumor comprises sarcomas and carcinomas.

3. The method of claim 2, wherein said bone tumor comprises metastatic bone tumor, osteosarcoma, and Neuroectodermal tumors.

4. The method of claim 1, wherein said bone tumor comprises of Ewing sarcoma.

5. The method of claim 1, wherein the collagen comprises of Type I collagen.

6. The method of claim 1, wherein said polysaccharide comprises hyaluronic acid, chondroitin sulfate, dermatan sulfate, keratan sulfate, heparan, heparan sulfate, dextran, dextran sulfate, or alginate.

7. The method of claim 6, wherein the polysaccharide comprises hyaluronic acid.

8. The method of claim 1, wherein said differentiation factor comprises members of the TGF-β super family.

9. The method of claim 8, wherein said differentiation factor comprises TGF-β.

10. The method of claim 8, wherein said differentiation factor is a bone morphogenic protein (BMP).

11. The method of claim 1, wherein said desired site of treatment is a surgical resection site of a bone tumor.

12. The method of claim 1, wherein said desired site of treatment is an osteolytic lesion.

13. A composition for the treatment of a bone tumor comprising an effective tumor-growth inhibiting amount of a matrix comprising collagen covalently cross-linked to an exogeneous polysaccharide wherein said polysaccharide is cross-linked to said collagen through oxidized sugar rings on said polysaccharide which forms covalent linkages to said collagen and a differentiation factor.

14. A composition according to claim 13, wherein said collagen comprises a Type I collagen.

15. A composition according to claim 13, wherein said polysaccharide comprises hyaluronic acid, chondroitic sulfate, dermaton sulfate, keraton sulfate, heparan, heparan sulfate, dextran, dextran sulfate or alginate.

16. A composition according to claim 15, wherein said polysaccharide comprises hyaluronic acid.

17. A composition according to claim 13, wherein said differentiation factor comprises a member of the TGF-β super family.

18. A composition according to claim 17, wherein said differentiation factor comprises TGF-β.

19. A composition according to claim 17, wherein said differentiation factor comprises bone morphogenic protein.

* * * * *